United States Patent [19]
Borromeo et al.

[11] Patent Number: 5,786,325
[45] Date of Patent: Jul. 28, 1998

[54] CYCLIC PEPTIDE ANTIFUNGAL AGENTS AND METHODS OF MAKING AND USING

[75] Inventors: Peter S. Borromeo, Fishers; William W. Turner, Jr., Bloomington, both of Ind.

[73] Assignee: Eli Lilly and Company, Indianapolis, Ind.

[21] Appl. No.: 614,949

[22] Filed: Mar. 11, 1996

Related U.S. Application Data

[63] Continuation of Ser. No. 451,337, May 26, 1995, abandoned.

[51] Int. Cl.$^6$ .............................. A61K 37/02; C07K 7/54
[52] U.S. Cl. ...................... 514/11; 514/9; 514/2; 530/317; 930/270
[58] Field of Search ............... 514/9, 11, 2; 530/317; 930/270, DIG. 548, DIG. 546

[56] References Cited

U.S. PATENT DOCUMENTS

| | | | |
|---|---|---|---|
| 4,293,488 | 10/1981 | Debono | 530/317 |
| 4,293,489 | 10/1981 | Debono | 530/317 |
| 4,320,052 | 3/1982 | Abbott et al. | 530/317 |
| 5,166,135 | 11/1992 | Schmatz | 530/317 |
| 5,514,651 | 5/1996 | Balkovec et al. | 514/11 |
| 5,516,756 | 5/1996 | Balkovec et al. | 514/11 |
| 5,541,160 | 7/1996 | Balkovec et al. | 514/11 |

FOREIGN PATENT DOCUMENTS

| | | |
|---|---|---|
| 359529 | 3/1990 | European Pat. Off. . |
| 447186 | 9/1991 | European Pat. Off. . |
| 448343 | 9/1991 | European Pat. Off. . |
| 448353 | 9/1991 | European Pat. Off. . |
| 448354 | 9/1991 | European Pat. Off. . |
| 448355 | 9/1991 | European Pat. Off. . |
| 448356 | 9/1991 | European Pat. Off. . |
| 462531 | 12/1991 | European Pat. Off. . |
| 503960 | 9/1992 | European Pat. Off. . |
| 525889 | 2/1993 | European Pat. Off. . |
| 561639 | 9/1993 | European Pat. Off. . |
| 2241956 | 9/1991 | United Kingdom . |
| 2242194 | 9/1991 | United Kingdom . |
| 9425045 | 11/1994 | WIPO . |
| 9425048 | 11/1994 | WIPO . |
| 9425050 | 11/1994 | WIPO . |

*Primary Examiner*—Chhaya D. Sayala
*Attorney, Agent, or Firm*—Janet T. McClain; David E. Boone

[57] ABSTRACT

Provided are pharmaceutical formulations, and methods of inhibiting fungal and parasitic activity using a compound of formula I

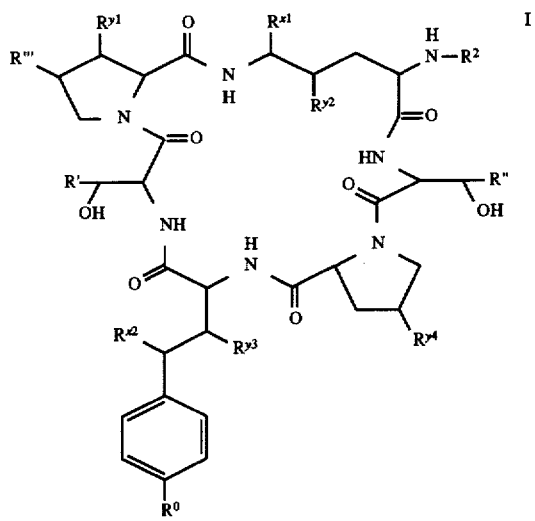

where:

$R'$, $R''$, $R'''$, $R^{x1}$, $R^{x2}$, $R^{y1}$, $R^{y2}$, $R^{y3}$, $R^{y4}$, and $R^0$ are as defined above; and $R^2$ is

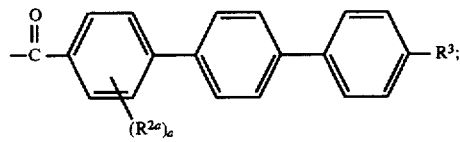

each $R^{2a}$ is independently hydroxy, halo, nitro, amino, trifluoromethyl, $C_1$–$C_6$ alkyl, $C_1$–$C_6$ alkoxy or $C_1$–$C_6$ alkylthio;

a is 1, 2, 3 or 4;

$R^3$ is $C_1$–$C_{12}$ alkyl, $C_1$–$C_{12}$ alkoxy or —O—$(CH_2)_m$—[O—$(CH_2)_n]_p$—O—$(C_1$–$C_{12}$ alkyl);

m is 2, 3 or 4;

n is 2, 3 or 4; and p is 0 or 1;

or a pharmaceutically acceptable salt thereof.

30 Claims, No Drawings

5,786,325

CYCLIC PEPTIDE ANTIFUNGAL AGENTS AND METHODS OF MAKING AND USING

This application is a continuation of application Ser. No. 08/451,337, filed on May 26, 1995 abandoned.

BACKGROUND OF THE INVENTION

This invention relates to semi-synthetic cyclic peptide compounds which are useful as antifungal and antiparasitic agents and which have improved stability and water solubility. In particular, it relates to derivatives of the echinocandin class of cyclic peptides, to methods for treating fungal and parasitic infections, and to formulations useful in the methods.

The compounds provided by this invention are semi-synthetic compounds derived from cyclic peptides which are produced by culturing various microorganisms. A number of cyclic peptides are known in the art including echinocandin B (A30912A), aculeacin, mulundocandin, sporiofungin, L-671,329, and S31794/F1.

In general, these cyclic peptides may be structurally characterized as a cyclic hexapeptide core (or nucleus) with an acylated amino group on one of the core amino acids. The amino group is typically acylated with a fatty acid group forming a side chain off the nucleus. For example, echinocandin B has a linoleoyl side chain while aculeacin has a palmitoyl side chain.

The fatty acid side chains may be removed from the cyclic peptide core to provide an amino nucleus (for example, a compound of formula I, below, where $R^2$ is hydrogen). The amino group may then be re-acylated to provide semi-synthetic compounds such as those claimed in the present application.

The echinocandin B nucleus has been re-acylated with certain non-naturally occurring side chain moieties to provide a number of antifungal agents (see, Debono, U.S. Pat. No. 4,293,489). Among such antifungal agents is cilofungin which is represented by a compound of formula IA where R', R" and R''' are methyl, $R^{x1}$, $R^{x2}$, $R^{y1}$, $R^{y2}$, $R^{y3}$, $R^{y4}$ and $R^0$ are each hydroxy and $R^2$ is p-(octyloxy)benzoyl.

SUMMARY OF THE INVENTION

The present invention provides a compound of formula I

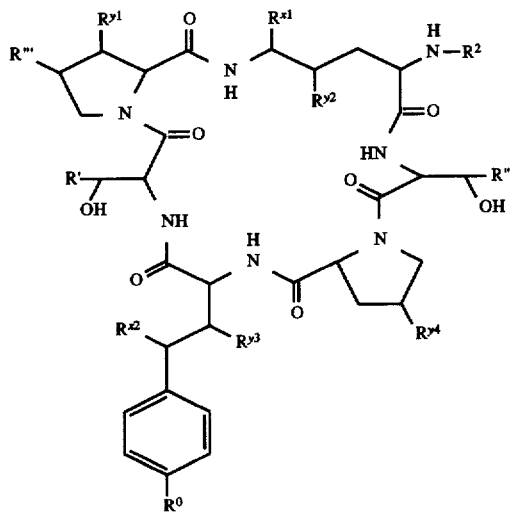

wherein:

R' is hydrogen, methyl or —CH$_2$C(O)NH$_2$;

R" and R''' are independently methyl or hydrogen;

$R_{x1}$ is hydrogen, hydroxy or —O—R;

R is $C_1$–$C_6$ alkyl, benzyl, —(CH$_2$)$_2$Si(CH$_3$)$_3$, —CH$_2$CHOHCH$_2$OH, —CH$_2$CH=CH$_2$, —(CH$_2$)$_a$COOH, —(CH$_2$)$_b$NR$^{z1}$R$^{z2}$, —(CH$_2$)$_c$POR$^{z3}$R$^{z4}$ or —[(CH$_2$)$_2$O]$_d$—(C$_1$–C$_6$) alkyl;

a, b and c are independently 1, 2, 3, 4, 5 or 6;

$R^{z1}$ and $R^{z2}$ are independently hydrogen, $C_1$–$C_6$ alkyl, or $R^{z1}$ and $R^{z2}$ combine to form —CH$_2$(CH$_2$)$_e$CH$_2$—;

$R^{z3}$ and $R^{z4}$ are independently hydroxy or $C_1$–$C_6$ alkoxy;

d is 1 or 2;

e is 1, 2 or 3;

$R^{x2}$, $R^{y1}$, $R^{y2}$, $R^{y3}$ and $R^{y4}$ are independently hydroxy or hydrogen;

$R^0$ is hydroxy, —OP(O)(OH)$_2$ or a group of the formulae:

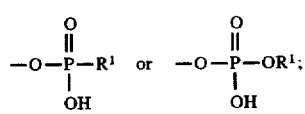

$R^1$ is $C_1$–$C_6$ alkyl, phenyl, p-halo-phenyl, p-nitrophenyl, benzyl, p-halo-benzyl or p-nitro-benzyl;

$R^2$ is

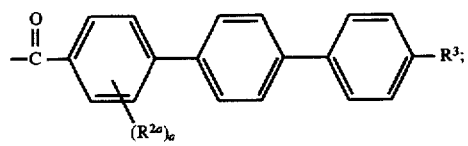

each $R^{2a}$ is independently hydroxy, halo, nitro, amino, trifluoromethyl, $C_1$–$C_6$ alkyl, $C_1$–$C_6$ alkoxy or $C_1$–$C_6$ alkylthio;

a is 1, 2, 3 or 4;

$R^3$ is $C_1$–$C_{12}$ alkyl, $C_1$–$C_{12}$ alkoxy or —O—(CH$_2$)$_m$—[O—(CH$_2$)$_n$]$_p$—O—(C$_1$–C$_{12}$ alkyl);

m is 2, 3 or 4;

n is 2, 3 or 4; and p is 0 or 1;

or a pharmaceutically acceptable salt thereof.

Also provided are pharmaceutical formulations, methods for inhibiting parasitic or fungal activity and methods of treating fungal or parasitic infections which employ the compounds of the invention.

DETAILED DESCRIPTION

As used herein, the term "$C_1$–$C_{12}$ alkyl" refers to a straight or branched alkyl chain having from one to twelve carbon atoms. Typical $C_1$–$C_{12}$ alkyl groups include methyl, ethyl, propyl, isopropyl, butyl, sec-butyl, t-butyl, pentyl, 5-methylpentyl, hexyl, heptyl, 3,3-dimethylheptyl, octyl, 2-methyl-octyl, nonyl, decyl, undecyl, dodecyl and the like. The term "$C_1$–$C_{12}$ alkyl" includes within its definition the terms "$C_1$–$C_6$ alkyl" and $C_1$–$C_4$ alkyl."

The term "halo" refers to chloro, fluoro, bromo or iodo.

The term "$C_1$–$C_{12}$ alkylthio" refers to a straight or branched alkyl chain having from one to twelve carbon atoms attached to a sulfur atom. Typical $C_1$–$C_{12}$ alkylthio groups include methylthio, ethylthio, propylthio, isopropylthio, butylthio, 3-methyl-heptylthio, octylthio, 5,5-dimethylhexylthio and the like.

The term "$C_1$–$C_2$ alkoxy" refers to a straight or branched alkyl chain having from one to twelve carbon atoms attached to an oxygen atom. Typical $C_1$–$C_{12}$ alkoxy groups include methoxy, ethoxy, propoxy, butoxy, sec-butoxy, pentoxy, 5-methyl-hexoxy, heptoxy, octyloxy, decyloxy dodecyloxy and the like. The term "$C_1$–$C_{12}$ alkyl" includes within its definition the terms "$C_1$–$C_6$ alkoxy" and $C_1$–$C_4$ alkoxy."

The term "hydroxy protecting group" refers to a substituent of an hydroxy group that is commonly employed to block or protect the hydroxy functionality while reactions are carried out on other functional groups on the compound. Examples of such hydroxy protecting groups include tetrahydropyranyl, 2-methoxyprop-2-yl, 1-ethoxyeth-1-yl, methoxymethyl, β-methoxyethoxymethyl, methylthiomethyl, t-butyl, t-amyl, trityl, 4-methoxytrityl, 4,4'-dimethoxytrityl, 4,4',4"-trimethoxytrityl, benzyl, allyl, trimethylsilyl, trimethylsilylethyl, (t-butyl)dimethylsilyl, and 2,2,2-trichloroethoxycarbonyl and the like. The species of hydroxy protecting group is not critical so long as the derivatized hydroxy group is stable to the conditions of the subsequent reaction(s) and can be removed at the appropriate point without disrupting the remainder of the molecule. A preferred hydroxy protecting group is trimethylsilylethyl. Further examples of hydroxy protecting groups are described in T. W. Greene, "Protective Groups in Organic Synthesis," John Wiley and Sons, New York, N.Y., (2nd ed., 1991) chapters 2 and 3. The term "protected hydroxyl" refers to a hydroxy group bonded to one of the above hydroxy protecting groups.

The term "amino protecting group" as used in the specification refers to substituents of the amino group commonly employed to block or protect the amino functionality while reacting other functional groups on the compound. Examples of such amino protecting groups include formyl, trityl, phthalimido, trichloroacetyl, chloroacetyl, bromoacetyl, iodoacetyl groups, or urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, t-butoxycarbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)-prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2-(methylsulfonyl)ethoxycarbonyl, 2-(triphenylphosphino)-ethoxycarbonyl, fluorenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like; benzoylmethylsulfonyl, 2-nitrophenylsulfenyl, diphenylphosphine oxide and like amino protecting groups. The species of amino protecting group employed is not critical so long as the derivatized amino group is stable to the condition of subsequent reaction(s) on other positions of the intermediate molecule and can be selectively removed at the appropriate point without disrupting the remainder of the molecule including any other amino protecting group(s). Preferred amino protecting groups are t-butoxycarbonyl (t-Boc), allyloxycarbonyl and benzyloxycarbonyl (CbZ). Further examples of groups referred to by the above terms are described by J. W. Barton, "Protective Groups in Organic Chemistry", J. G. W. McOmie, Ed., Plenum Press, New York, N.Y., 1973, Chapter 2, and T. W. Greene, "Protective Groups in Organic Synthesis", John Wiley and sons, New York, N.Y., 1981, Chapter 7.

The term "inhibiting", i.e. a method of inhibiting parasitic or fungal activity, includes stopping, retarding or prophylactically hindering or preventing the growth or any attending characteristics and results from the existence of a parasite or fungus.

The term "contacting", i.e. contacting a compound of the invention with a parasite or fungus, includes a union or junction, or apparent touching or mutual tangency of a compound of the invention with a parasite or fungus. However, the term does not imply any further limitations to the process, such as by mechanism of inhibition, and the methods are defined to encompass the spirit of the invention, which is to inhibit parasitic and fungal activity by the action of the compounds and their inherent antiparasitic and antifungal properties, or in other words, the compounds, used in the claimed methods are the causative agent for such inhibition.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a mineral or organic acid or an inorganic base. Such salts are known as acid addition and base addition salts.

Acids commonly employed to form acid addition salts are mineral acids such as hydrochloric acid, hydrobromic acid, hydroiodic acid, sulfuric acid, phosphoric acid and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

Preferred compounds of this invention are those compounds of formula I where:

R', R" and R'" are each methyl;

$R^{y1}$, $R^{y2}$, $R^{y3}$ and $R^{y4}$ are each hydroxy;

$R^{x1}$ is hydrogen, hydroxy or —O—R;

R is methyl, benzyl, —CH$_2$CHOHCH$_2$OH, —(CH$_2$)$_b$NR$^{z1}$R$^{z2}$ or —(CH$_2$)$_2$POR$^{z3}$R$^{z4}$;

b is 2, 3, 4, 5 or 6;

$R^{z1}$ and $R^{z2}$ are independently hydrogen or $C_1$–$C_4$ alkyl;

$R^{z3}$ and $R^{z4}$ are independently hydroxy or methoxy;

$R^{x2}$ is hydrogen or hydroxy;

$R^0$ is hydroxy, —OP(O)(OH)$_2$ or a group of the formulae:

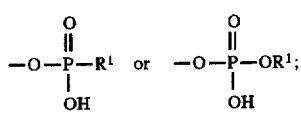

$R^1$ is methyl;

or a pharmaceutically acceptable salt thereof.

Of these compounds, more preferred are those compounds of formula I where:

$R^{x1}$ is hydrogen or hydroxy;

$R^{x2}$ is hydrogen or hydroxy;

$R^0$ is hydroxy;

a is 1 or 2;

$R^{2a}$ is halo, $C_1$–$C_6$ alkyl or $C_1$–$C_6$ alkoxy; and $R^3$ is $C_1$–$C_{12}$ alkoxy or —O—(CH$_2$)$_2$—O—(C$_1$–C$_{12}$ alkyl);

or a pharmaceutically acceptable salt thereof.

Of these compounds, further preferred are those compounds of formula I where:

$R^{x1}$ is hydroxy;

$R^{x2}$ is hydroxy;

a is 1;

$R^{2a}$ is methyl, chloro, fluoro or methoxy;

$R^3$ is $C_1$–$C_6$ alkoxy;

or a pharmaceutically acceptable salt thereof.

Of these compounds, the most preferred are those compounds where:

$R^2$ is

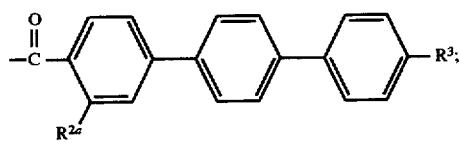

$R^{2a}$ is methyl, chloro or fluoro;

or a pharmaceutically acceptable salt thereof.

The compounds of formula I may be prepared according to Reaction Scheme I, as follows.

Reaction Scheme I

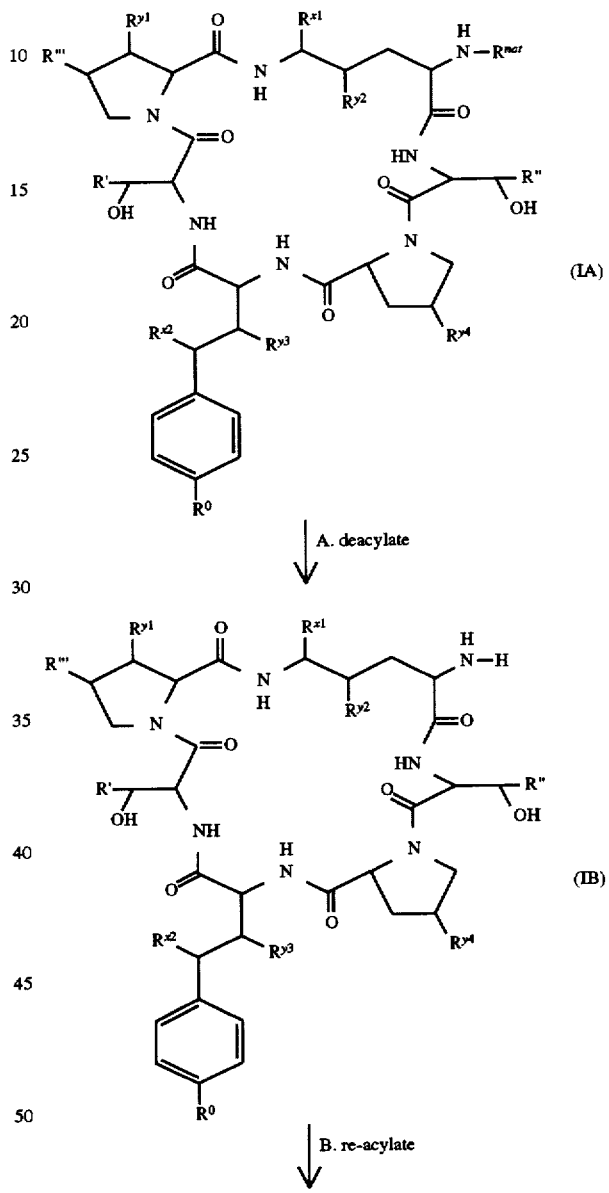

-continued
Reaction Scheme I

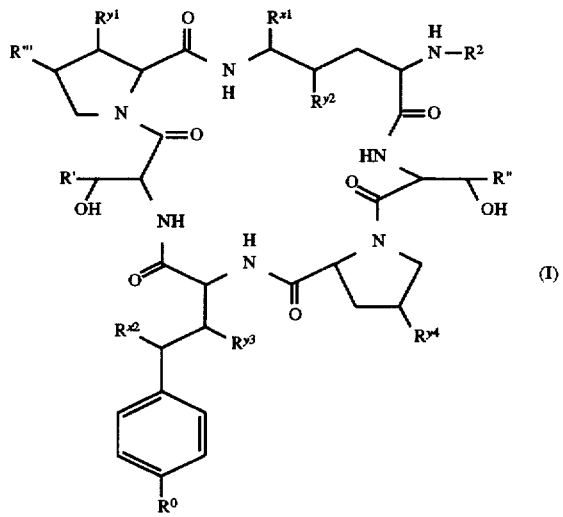

(I)

wherein:

R$^{nat}$ is a naturally occurring cyclic peptide sidechain; and R', R", R'", R$^{x1}$, R$^{x2}$, R$^{y1}$, R$^{y2}$, R$^{y3}$, R$^{y4}$, R$^{0}$ and R$^{2}$ are as defined above.

Reaction scheme I, above, is carrying accomplished by carrying out reactions A and B, above. Once a reaction is complete, the intermediate compound may be isolated by procedures well-known in the art, for example, the compound may be crystallized or precipitated and then collected by filtration, or the reaction solvent may be removed by extraction, evaporation or decantation. The intermediate compound may be further purified, if desired, by common techniques such as crystallization or precipitation or chromatography over solid supports such as silica gel, alumina and the like, before carrying out the next step of the reaction scheme.

In reaction IA, a naturally occurring cyclic peptide of the formula IA is deacylated using procedures known in the art to provide an amino nucleus of formula IB. This reaction is typically carried out using enzymatic deacylation by exposing the naturally occurring cyclic peptide to a deacylase enzyme. The deacylase enzyme may be obtained from the microorganism Actinoplanes utahensis and used substantially as described in U.S. Pat. Nos. 4,293,482 and 4,304,716, herein incorporated by reference. The deacylase enzyme may also be obtained from the Pseudomonas species. Deacylation may be accomplished using whole cells of Actinoplanes utahensis or Pseudomonas or the crude or purified enzyme thereof or using an immobilized form of the enzyme. See European Patent Application No. 0 460 882 (Dec. 11, 1991). Examples of naturally occurring cyclic peptides which may be used as starting materials include aculeacin (palmitoyl side chain), tetrahydroechinocandin B (stearoyl side chain), mulundocandin (branched C$_{15}$ side chain), L-671,329 (C$_{16}$ branched side chain), S 31794/F1 (tetradecanoyl side chain), sporiofungin (C$_{15}$ branched side chain), FR901379 (palmitoyl side chain) and the like. A preferred naturally occurring cyclic peptide is echinocandin B (a compound of formula IA where R', R" and R'" are each methyl, R$^{x1}$, R$^{x2}$, R$^{y1}$, R$^{y2}$, R$^{y3}$, R$^{y4}$ and R$^{0}$ are each hydroxy and R$^{2}$ is linoleoyl).

In Reaction IB, the amino nucleus of formula IB is then re-acylated using procedures known in the art to provide a compound of formula I where R$^{0}$ is hydroxy; R$^{x1}$ is hydroxy; and R$_{2}$ is an acyl group as defined hereinabove.

For example, the amino nucleus may be acylated by reaction with an appropriately substituted acyl halide, preferably in the presence of an acid scavenger such as a tertiary amine, such as triethylamine. The reaction is typically carried out at a temperature of from about −20° C. to about 25° C. Typical solvents for this reaction include polar aprotic solvents such as dioxane or dimethylformamide. Solvent choice is not critical so long as the solvent employed is inert to the ongoing reaction and the reactants are sufficiently solubilized to effect the desired reaction.

The amino nucleus may also be acylated by reaction with an appropriately substituted carboxylic acid, in the presence of a coupling agent. Typical coupling agents include dicyclohexylcarbodiimide (DCC), N,N'-carbonyldiimidazole, bis(2-oxo-3-oxazolidinyl)phosphinic chloride (BOP-Cl), N-ethoxycarbonyl-2-ethoxy-1,2-dihydroquinoline (EEDQ), benzotriazol-1-yloxytripyrrolidinophosphonium hexafluorophosphate (PYBOP) and the like.

In addition, the amino nucleus may be acylated with an activated ester of a carboxylic acid such as an ester of a carboxylic acid of the formula R$^{2}$—COOH and p-nitrophenyl, 2,4,5-trichlorophenyl, hydroxybenzotriazole hydrate (HOBT.H$_{2}$O), pentafluorophenol, N-hydroxysuccinimide and the like. Preferred acylating moieties are the active esters of the carboxylic acid R$^{2}$—COOH such as a benzotriazole ester. The reaction is typically carried out for one to sixty five hours at a temperature from about 0° C. to about 30° C. in an aprotic solvent. The reaction is generally complete after about twenty four to forty eight hours when carried out a temperature of from about 15° C. to about 30° C. Typical solvents for this reaction are tetrahydrofuran and dimethylformamide or a mixture of such solvents. The amino nucleus is generally employed in equimolar proportions relative to the activated ester or with a slight excess of the amino nucleus.

The compounds of formula I where R$^{x1}$ is hydroxy may be reacted with an appropriately substituted alcohol in the presence of an acid to provide a compound of formula I where R$^{x1}$ is —O—R, where R is C$_{1}$-C$_{6}$ alkyl, benzyl, —(CH$_{2}$)$_{2}$Si(CH$_{3}$)$_{3}$, —CH$_{2}$CH=CH$_{2}$, —(CH$_{2}$)$_{a}$COOH, —(CH$_{2}$)$_{b}$NR$^{z1}$R$^{z2}$, —(CH$_{2}$)$_{c}$POR$^{z3}$R$^{z4}$ or —[(CH$_{2}$)$_{2}$O]$_{d}$—(C$_{1}$-C$_{6}$)alkyl. The reaction is typically carried out in a polar aprotic solvent such as dioxane or dimethylsulfoxide at a temperature of from about 0° C. to about 35° C., preferably at about room temperature. Solvent choice is not critical so long as the solvent employed is inert to the ongoing reaction and the reactants are sufficiently solubilized to effect the desired reaction. Preferred acids include p-toluenesulfonic acid, hydrochloric acid and camphorsulfonic acid.

The compounds of formula I where R$^{x1}$ is —(CH$_{2}$)$_{b}$NR$^{z1}$R$^{z2}$ where R$^{z1}$ and R$^{2}$ are hydrogen may be prepared via a protected compound wherein R$^{x1}$ is —(CH$_{2}$)$_{b}$NHR$^{a}$ where R$^{a}$ is an amino protecting group. The resultant protected compound is then deprotected according to procedures known in the art.

The compounds of formula I where R$^{x1}$ is —CH$_{2}$CHOHCH$_{2}$OH may be prepared by hydroxylating a compound of formula I where R$^{x1}$ is —CH$_{2}$CH=CH$_{2}$ with osmium tetroxide in the presence of a catalyst at a temperature in the range of from about 0° C. to about 40° C. for about one to twenty four hours in a organic/aqueous solvent mixture, for example dioxane/water. Suitable catalysts include N-methylmorpholine N-oxide (NMO) and the like. Typical solvents suitable for use in this reaction include dimethylformamide, tetrahydrofuran, acetone and dioxane. Solvent choice is not critical so long as the solvent employed is inert to the ongoing reaction and the reactants are sufficiently solubilized to effect the desired reaction. The reaction is preferably conducted at a temperature in the range of from about 200° C. to about 30° C. for about eighteen to twenty four hours.

The compounds of formula I where $R^o$ is hydroxy may be phosphorylated by reaction with an appropriately substituted alkyl or phenyl phosphate to provide a compound of formula I where $R^o$ is —O—P(O)OH—$R^1$ where $R^1$ is $C_1$-$C_6$ alkoxy or phenoxy, or by reaction with an appropriately substituted alkyl or phenyl phosphonic acid to provide a compound of formula I where $R^o$ is —O—P(O)OH—$R^1$ where $R^1$ is $C_1$-$C_6$ alkyl, or an appropriately substituted phenyl or benzyl moiety, to provide a compound of formula I where $R^o$ is a group of the formula —OP(O)OH—$R^1$. The phosphonic acid is typically used in an activated form, for example as a phosphonic halide, preferably a phosphonic chloride. The reaction is carried out in the presence of a base such as lithium trimethylsilanolate (LiOTMS), lithium bis (trimethylsilyl)amide (LHMDS), pyridine and the like. The reaction is typically carried out for up to one hour at a temperature from about –30° C. to about 0° C. in an aprotic solvent such as tetrahydrofuran and dimethylformamide. The reaction is generally complete in about fifteen minutes when carried out under these conditions. The phosphate or phosphonate reactant is generally employed in equimolar proportions to about a one mole excess relative to the amino nucleus in the presence of an equimolar or slight excess of the base. Phosphorylation of an amino nucleus with unprotected aminal hydroxy groups is typically carried out at lower temperatures, for example from about –30° C. to about –15° C.

Alternatively, the aminal hydroxy moieties on the compound of formula I are optionally protected with an hydroxy protecting group using procedures known in the art. For example, the reaction is typically carried out by combining the compound of formula I with a suitable hydroxy protecting group in the presence of a catalyst at a temperature in the range of from about 0° C. to about 40° C. for about one to five hours in a mutual inert solvent. The hydroxy protecting group is generally employed in an amount ranging from about equimolar proportions to about a 100 molar excess relative to the compound of formula I, preferably in a large molar excess. Suitable catalysts include strong acids such as p-toluenesulfonic acid, camphorsulfonic acid (CSA), hydrochloric acid, sulfuric acid, trifluoroacetic acid and the like. Typical solvents suitable for use in this reaction include any organic solvent such as dioxane. Solvent choice is not critical so long as the solvent employed is inert to the ongoing reaction and the reactants are sufficiently solubilized to effect the desired reaction. The reaction is preferably conducted at a temperature in the range of from about 20° C. to about 30° C. for about two to four hours. The protected compound of formula I is then phosphorylated as described above. The hydroxy protecting group(s) are then removed according to procedures known in the art to provide a phosphorylated compound of formula I. For example, the protecting groups can be removed by reaction with a Lewis acid in a mutual inert organic solvent such as methylene chloride. Examples of Lewis acids include trimethylsilylbromide, boron trifluoride etherate and the like. The reaction is typically carried out at a temperature of from about 0° C. to about 40° C., preferably at a temperature of from about 20° C. to about 30° C. A preferred Lewis acid is boron trifluoride etherate.

The dideoxy compounds of formula I are prepared by removing the benzylic and aminal hydroxy groups ($R^{x2}$ and $R^{x1}$, respectively). The hydroxy groups may be removed by subjecting a non-dideoxy compound of formula I (where $R_2$ is hydrogen or acyl) to a strong acid and a reducing agent at a temperature of between –5° C. and 70° C., in a suitable solvent. Typical strong acids include trichloroacetic acid, trifluoroacetic acid or borontrifluoride etherate. A preferred strong acid is trifluoroacetic acid. Typical reducing agents include sodium cyanoborohydride or triethylsilane. A preferred reducing agent is triethylsilane. Suitable solvents include methylene chloride, chloroform or acetic acid, preferably methylene chloride. The strong acid should be present in an amount of from 2 to 80 mol per mol of substrate, and the reducing agent should be present in an amount of 2 to 80 mol per mol of substrate. This process affords selective removal of the aminal and benzylic hydroxy groups.

The cyclic peptides used to make the compounds of the present invention may be prepared by fermentation of known microorganisms. For example, the cyclic peptide of formula IB where R', R" and R'" are methyl, $R^{x1}$, $R^{x2}$, $R^{y1}$, $R^{y2}$, $R^{y3}$, $R^{y4}$ and $R^o$ are each hydroxy (cyclic nucleus corresponding to A-30912A) may be prepared using the procedure detailed in Abbott et al., U.S. Pat. No. 4,293,482, which is herein incorporated by reference. The cyclic peptide of formula IB where R', R" and R'" are methyl, $R^{x1}$ is hydroxy, $R^{x2}$ is hydrogen, $R^{y1}$, $R^{y2}$, $R^{y3}$, $R^{y4}$ and $R^o$ are each hydroxy (cyclic nucleus corresponding to A-30912B) may be prepared using the procedure detailed in Abbott et al., U.S. Pat. No. 4,299,763, which is herein incorporated by reference. Aculeacin may be prepared using the procedure detailed in Mizuno et al., U.S. Pat. No. 3,978,210 which is herein incorporated by reference. The cyclic peptide of formula IB where R' is —CH$_2$C(O)NH$_2$, R" is methyl, R'" is hydrogen, $R^{x1}$, $R^{x2}$, $R^{y1}$, $R^{y2}$, $R^{y3}$, $R^{y4}$ and $R^o$ are each hydroxy may be prepared by deacylating the cyclic peptide prepared using the procedure detailed in Chen et al., U.S. Pat. No. 5,198,421, which is herein incorporated by reference.

The $R^2$—COOH precursor acids are prepared by reacting an appropriately substituted biphenyl boronic acid reactant with an appropriately substituted p-halobenzoic acid reactant in the presence of a catalyst such as tetrakis (triphenylphosphine)palladium and an inorganic base such as potassium carbonate. The reaction is typically carried out with equimolar proportions of the boronic acid reactant and the p-benzoic acid reactant, or a slight molar excess of the benzoic acid reactant relative to the boronic acid reactant, and a 1–2 molar excess of the inorganic base in a mutual inert organic solvent such as toluene at a temperature of from about 20° C. to the reflux temperature of the reaction mixture. The reaction is generally complete after about four to about ten hours when carried out at reflux temperature in toluene.

The boronic acid reactant may be prepared by reacting an appropriately substituted halobiphenyl reactant with two equivalents of triisopropyl borate in the presence of a slight molar excess of an alkyl lithium, for example sec-butyl lithium, relative to the halobiphenyl reactant in a mutual inert solvent such as tetrahydrofuran. The alkyl lithium is typically combined with the solvent by dropwise addition at reduced temperatures (<–70° C.) and allowed to stir for approximately thirty minutes before the addition of the triisopropyl borate. The reaction is typically carried out initially at a temperature of from about –100° C. to about –50° C., preferably from about –75° C. to about –85° C. for thirty minutes to two hours and then warmed to room temperature and reacted for an additional one to three hours. The reaction is generally complete in from several minutes to about four hours. When the reaction is substantially complete, the boronic acid moiety is formed by the addition of an acid. A preferred acid is a 1N hydrochloric acid solution.

The resultant carboxylic acid is then converted to an activated ester, preferably a benzotriazole ester, which is used to acrylate the cyclic peptide nucleus as described above. For example, the carboxylic acid may be converted to the corresponding benzotriazole ester by combining the carboxylic acid with N-methanesulfonate-benzotriazole in a mutual inert solvent such as dimethylformamide or with hydroxybenzotriazole hydrate (HOBT.H$_2$O) and a coupling agent such as N,N'-dicyclohexylcarbodiimide (DCC) in a mutual inert solvent such as methylene chloride.

The following Preparations and Examples further describe how to synthesize the compounds of the present invention. The terms melting point, proton nuclear magnetic resonance spectra, mass spectra, infrared spectra, ultraviolet spectra, elemental analysis, high performance liquid chromatography, and thin layer chromatography are abbreviated "m.p.", "NMR", "MS", "IR", "UV", "Analysis", "HPLC" and "TLC", respectively. In addition, the absorption maxima listed for the IR spectra are only those of interest and not all of the maxima observed.

PREPARATION 1

A

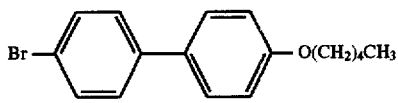

A solution containing 50 g (200 mmol) of 4-bromophenol, 33.5 g (298 mmol) of potassium t-butoxide and 40 ml (298 mmol) of 1-iodopentane in 1000 ml of tetrahydrofuran was reacted at reflux temperature for approximately twenty four hours. When the reaction was substantially complete, as indicated by thin layer chromatography (TLC) the reaction was filtered. The resultant filtrate was concentrated in vacuo to provide a purple solid. This solid was redissolved in a water/diethyl ether mixture to provide a yellow solution. This solution was washed sequentially with 200 ml of water (twice), 100 ml of 2N sodium hydroxide (twice) and 200 ml of brine (twice), dried over sodium sulfate and then concentrated in vacuo to provide a yellow powder. This solid was recrystallized from hot hexanes to provide a white powder.

Yield: 45.8 mg (72%).

B

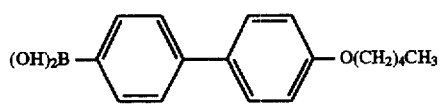

To a cold (−78° C.) solution of 10.0 mg (42.9 mmol) of 29 g (90.8 mmol) of the compound of Preparation 1A, was added 91 ml of sec-butyllithium in 1000 ml of tetrahydrofuran (118 mmol), dropwise. To the resulting mixture was added 41.9 ml (181.7 mmol) of triisopropyl borate, dropwise. The resultant reaction mixture was stirred for approximately thirty minutes and then warmed to room temperature and allowed to react for approximately two hours. The reaction was then quenched by the addition of 1N hydrochloric acid. The resultant mixture was concentrated in vacuo to provide a residue. This residue was redissolved in diethyl ether, filtered and reduced to dryness to provide the desired subtitled compound.

PREPARATION 2

N-methanesulfonate benzotriazole

To a cold (5° C.) solution of 100 g (0.653 mol) of hydroxybenzotriazole (HOBT) in 750 ml of methylene chloride, was added 82.59 g (0.816 mol) of triethylamine while maintaining the temperature at 5°–10° C. followed by the addition of 82.28 g (0.718 mol) of methanesulfonyl chloride while maintaining the temperature at 4°–10° C. The resultant reaction mixture was reacted for approximately one hour at 4° C. When the reaction was substantially complete, as indicated by TLC, the reaction mixture was transferred to a separatory funnel and washed sequentially with water (three times) and a saturated sodium chloride solution, dried over sodium sulfate, filtered and concentrated in vacuo to provide a solid. This solid was combined with a small amount of diethyl ether and the resultant mixture was filtered and dried in vacuo to provide 126.2 g of a white crystalline solid.

Yield: 91%.

PREPARATION 3

A. 4-Bromo-2-chloro benzoic acid, methyl ester

Hydrochloric acid (gas) was bubbled through a solution of 10 g (42.5 mmol) of 4-bromo-2-chloro benzoic acid in 100 ml of methanol until reflux occurred. The resulting reaction mixture was allowed to react overnight. When the reaction was substantially complete, as indicated by TLC, the reaction mixture was concentrated in vacuo to provide a residue. This residue was redissolved in diethyl ether and washed sequentially with water (twice) and a saturated sodium chloride solution, dried over sodium sulfate, filtered and then concentrated in vacuo to provide 10 g of a light tan oil.

Yield: 94%.

B

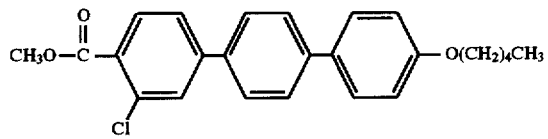

A solution of 3.24 mg (13.2 mmol) of the subtitled compound of Preparation 3A in 25 ml of methanol was added to a solution containing 3 g (10.5 mmol) of the compound of Preparation 1B, 30 ml of 2N sodium carbonate and 1.2 g (1.0 mmol) of tetrakis(triphenylphosphine) palladium in 60 ml of benzene, under nitrogen. The resultant reaction mixture was allowed to react at reflux temperature for approximately three hours. When the reaction was substantially complete, as indicated by TLC, the biphasic mixture was separated and the organic layer was washed sequentially with water and brine, dried over magnesium sulfate, filtered and concentrated in vacuo to provide a solid. This solid was recrystallized from hot hexanes.

MS(FD): 344(M$^+$).

Yield: 83%.

C

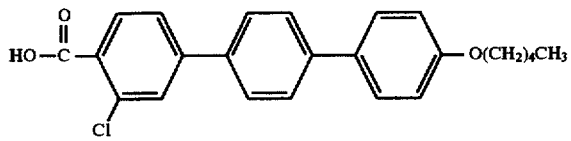

A mixture of 3.1 g (7.6 mmol) of the subtitled compound of Preparation 3B and 15 ml of a 1N aqueous sodium hydroxide solution in 35 ml of dioxane was refluxed for approximately four hours. When the reaction was substantially complete, as indicated by TLC, the reaction mixture was diluted with water and filtered. The precipitate was washed with water and then dried in vacuo to provide 2.98 g of a white solid.

Yield: quantitative.

D

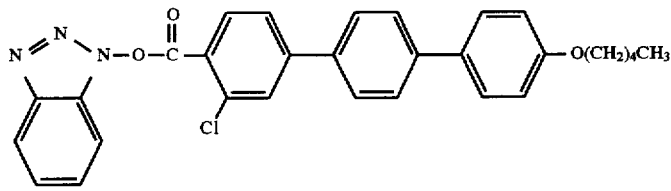

To a mixture of 2.9 g (7.4 mmol) of the subtitled compound of Preparation 3C in 60 ml of anhydrous dimethylformamide, was added the subtitled compound of Preparation 2, followed by 0.82 g (8.16 mmol) of triethylamine. After reacting overnight at room temperature, the reaction mixture was concentrated in vacuo to provide a yellow solid. This solid was dissolved in methylene chloride and washed twice with water, dried over sodium sulfate, filtered and then concentrated in vacuo to provide a solid. This solid was washed with diethyl ether and then dried in vacuo to provide 2.7 g of the desired compound.

Yield: 71%.

MS(FD): 511 (M).

Analysis for $C_{30}H_{26}N_3O_3Cl$: Calcd: C, 70.38; H, 5.12; N, 8.21; Found: C, 71.72; H, 5.40; N, 6.87.

The following compounds (Preparations 4–7) were prepared substantially in accordance with the procedures detailed in Preparations 3A–D.

Yield: 2 g (63%).

MS(FD): 491 (M).

Analysis for $C_{31}H_{29}N_3O_3$: Calcd: C, 75.74; H, 5.95; N, 8.55; Found: C, 75.95; H, 6.01; N, 8.70.

PREPARATION 4

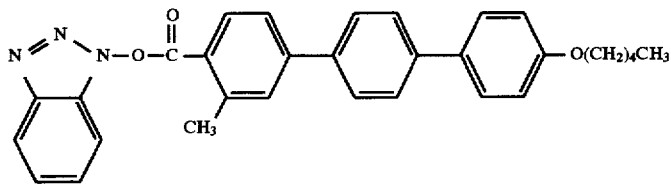

Yield: 3 g (91%).
MS(FD): 491 (M).
Analysis for $C_{31}H_{29}N_3O_3$: Calcd: C, 75.74; H, 5.95; N, 8.55; Found: C, 77.80; H, 6.11; N, 8.89.

PREPARATION 5

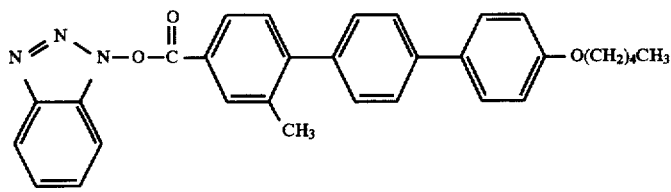

PREPARATION 6

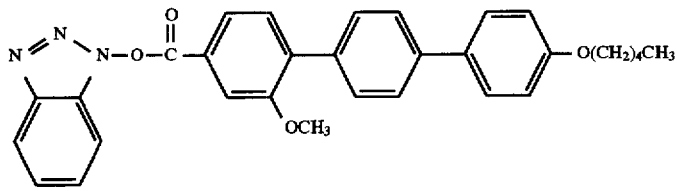

Yield: 2.05 g.

MS(FD): 507 (M).

Analysis for $C_{31}H_{29}N_3O_4$: Calcd: C, 73.36; H, 5.76; N, 8.28; Found: C, 73.56; H, 5.68; N, 8.52.

PREPARATION 7

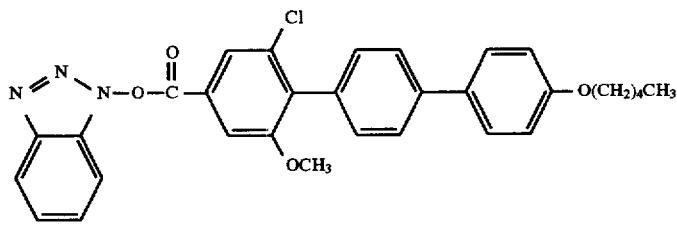

Yield: 400 mg.

PREPARATION 8

A

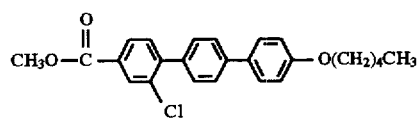

The subtitled compound was prepared substantially in accordance with the procedures detailed in Preparations 3A–B.

B

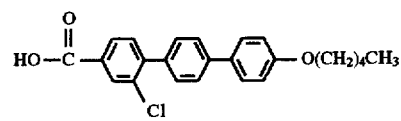

To a solution of 2.5 g (6.1 mmol) of the subtitled compound of Preparation 8A in dioxane, was added 0.73 g (30.5 mmol) of lithium hydroxide in 15 ml of water. The resultant reaction mixture was refluxed for approximately three hours and then cooled to room temperature and concentrated in vacuo to provide a residue. This residue was partitioned between diethyl ether and water. The resulting layers were separated and the organic layer was filtered to provide a white solid. This solid was redissolved in hot dioxane and the resultant solution was acidified with 5N hydrochloric acid and then diluted with water resulting in the formation of a precipitate. This precipitate was isolated by filtration and dried in vacuo.

Yield: 2.3 g (95%).

m.p. 204°–206° C.

MS(FD): 394 (M).

Analysis for $C_{24}H_{23}O_3Cl$: Calcd: C, 73.00; H, 5.87; Found: C, 72.73; H, 5.79.

C

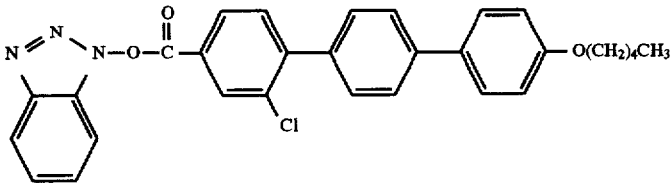

To a suspension of 2 g (5.06 mmol) of the subtitled compound of Preparation 8B in 100 ml of methylene chloride, was added 0.93 g (6.08 mmol) of hydroxybenzotriazole hydrate (HOBT.H₂O), followed by 1.25 g (6.08 mmol) of dicyclohexylcarbodiimide (DCC). After reacting overnight at room temperature, the reaction mixture was filtered and the resultant filtrate was concentrated in vacuo to provide a residue. This residue was combined with diethyl ether and the resultant mixture was filtered to provide 2.6 g of a white solid that was used without further purification.

PREPARATION 9

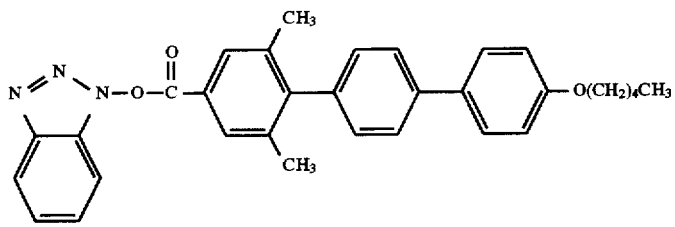

The desired titled compound was prepared substantially in accordance with the procedure detailed in Preparation 8.

Data for carboxylic acid

Yield: 2.3 g of a white solid (86%).

m.p. 232°–235° C.

MS (FD): 388 (M).

Analysis for $C_{26}H_{28}O_3$: Calcd: C, 80.38; H, 7.26; Found: C, 80.11; H, 7.10.

PREPARATION 10

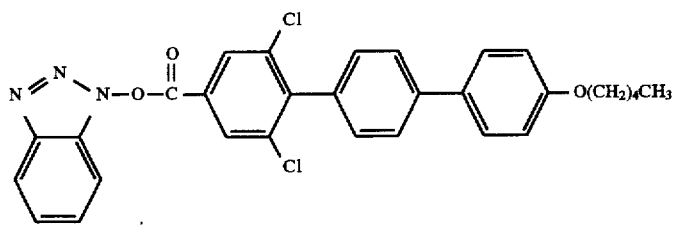

The desired titled compound was prepared substantially in accordance with the procedure detailed in Preparation 8.

Data for carboxylic acid

Yield: 2.1 g of a white solid (78%).

m.p. 226°–229° C.

MS(FD): 428 (M).

Analysis for $C_{24}H_{22}O_3Cl_2$: Calcd: C, 67.14; H, 5.17; Found: C, 67.24; H, 5.20.

PREPARATION 11

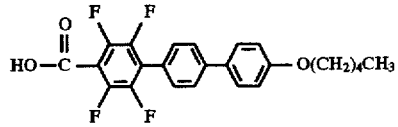

The desired titled compound was prepared substantially in accordance with the procedure detailed in Preparation 8B.

Yield: 2.8 g of a faint yellow solid (88%).

MS(FD): 432 (M).

Analysis for $C_{24}H_{20}O_3F_4$: Calcd: C, 66.66; H, 4.66; Found: C, 66.91; H, 4.86.

PREPARATION 12

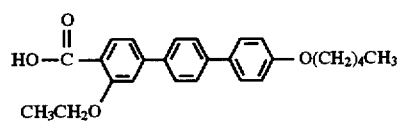

The desired titled compound was prepared substantially in accordance with the procedure detailed in Preparation 8B.

Yield: 3 g of a white, pearlescent solid (quantitative).

MS(FD): 404 (M).

Analysis for $C_{26}H_{28}O_4$: Calcd: C, 77.20; H, 6.98; Found: C, 73.92; H, 6.91.

PREPARATION 13

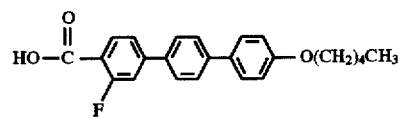

The desired titled compound was prepared substantially in accordance with the procedure detailed in Preparation 8B.

Yield: 2.2 g of a light tan solid (57%).

MS(FD): 378 (M).

Analysis for $C_{24}H_{23}O_3F$: Calcd: C, 76.17; H, 6.13; Found: C, 73.85; H, 6.07.

Example 1

Preparation of the compound of formula I where R', R" and R'" are each methyl, $R^{x1}$, $R^{x2}$, $R^{y1}$, $R^{y2}$, $R^{y3}$, $R^{y4}$ and $R^0$ are each hydroxy and $R^2$ is

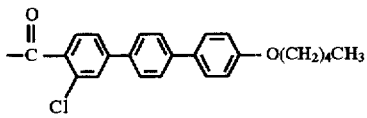

To a solution containing 1 g (1.25 mmol) of the compound of the (A-30912A) nucleus (compound of formula IB where R', R" and R'" are each methyl, $R^{x1}$, $R^{x2}$, $R^{y1}$, $R^{y2}$, $R^{y3}$ and $R^{y4}$ are each hydroxy and $R^0$ is hydroxy) in 120 ml of dimethylformamide, was added 0.71 g (1.38 mmol) of the subtitled compound of Preparation 3D. After stirring for approximately three days at room temperature, the reaction mixture was concentrated in vacuo to provide a residue. This residue was slurried in diethyl ether and isolated by filtration to provide a white solid. This solid was washed with methylene chloride, dissolved in 50 ml of methanol and then filtered. The resultant filtrate was combined with water resulting in the formation of a precipitate, acidified with glacial acetic acid, and then filtered to provide a solid. This solid was slurried in diethyl ether and the resultant mixture was decanted to provide a solid that was dried in vacuo to provide 0.8 g of the desired compound.

Yield: 50%.

High Res. MS(FAB) for $C_{58}H_{73}N_7O_{17}Cl$: Calcd: 1174.4751 Found: 1174.4748

Example 2

Preparation of the compound of formula I where R', R" and R'" are each methyl, $R^{x1}$, $R^{x2}$, $R^{y1}$, $R^{y2}$, $R^{y3}$, $R^{y4}$ and $R^0$ are each hydroxy and $R^2$ is

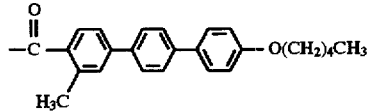

The titled compound was prepared substantially in accordance with the procedure detailed in Example 1, using 1 g (1.25 mmol) of the compound of the (A-30912A) nucleus (compound of formula IB where R', R" and R'" are each methyl, $R^{x1}$, $R^{x2}$, $R^{y1}$, $R^{y2}$, $R^{y3}$ and $R^{y4}$ are each hydroxy and $R^0$ is hydroxy), 0.68 g (1.38 mmol) of the compound of Preparation 4 in 120 ml of dimethylformamide.

Yield: 0.9 g.

High Res. MS(FAB) for $C_{59}H_{76}N_7O_{17}$: Calcd: 1154.5298 Found: 1154.5288

Example 3

Preparation of the compound of formula I where R', R" and R'" are each methyl, $R^{x1}$, $R^{x2}$, $R^{y1}$, $R^{y2}$, $R^{y3}$, $R^{y4}$ and $R^0$ are each hydroxy and $R^2$ is

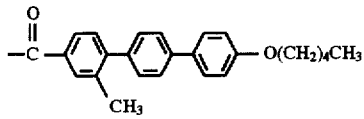

The titled compound was prepared substantially in accordance with the procedure detailed in Example 1, using 1 g (1.25 mmol) of the compound of the (A-30912A) nucleus (compound of formula IB where R', R" and R'" are each methyl, $R^{x1}$, $R^{x2}$, $R^{y1}$, $R^{y2}$, $R^{y3}$ and $R^{y4}$ are each hydroxy and $R^0$ is hydroxy), 0.68 g (1.38 mmol) of the compound of Preparation 5 in 120 ml of dimethylformamide.

Yield: 0.85 g.

High Res. MS(FAB) for $C_{59}H_{76}N_7O_{17}$: Calcd: 1154.5298 Found: 1154.5332

Example 4

Preparation of the compound of formula I where R', R" and R'" are each methyl, $R^{x1}$, $R^{x2}$, $R^{y1}$, $R^{y2}$, $R^{y3}$, $R^{y4}$ and $R^0$ are each hydroxy and $R^2$ is

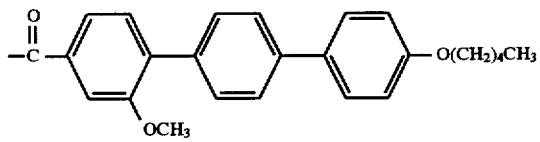

The titled compound was prepared substantially in accordance with the procedure detailed in Example 1, using 1 g (1.25 mmol) of the compound of the (A-30912A) nucleus (compound of formula IB where R', R" and R'" are each methyl, $R^{x1}$, $R^{x2}$, $R^{y1}$, $R^{y2}$, $R^{y3}$ and $R^{y4}$ are each hydroxy and $R^0$ is hydroxy), 0.7 g (1.37 mmol) of the compound of Preparation 6 in 100 ml of dimethylformamide.

Yield: 0.9 g.

High Res. MS(FAB) for $C_{59}H_{75}N_7O_{18}Li$: Calcd: 1176.5329 Found: 1176.5309 (M+Li$^+$)

Example 5

Preparation of the compound of formula I where R', R" and R'" are each methyl, $R^{x1}$, $R^{x2}$, $R^{y1}$, $R^{y2}$, $R^{y3}$, $R^{y4}$ and $R^0$ are each hydroxy and $R^2$ is

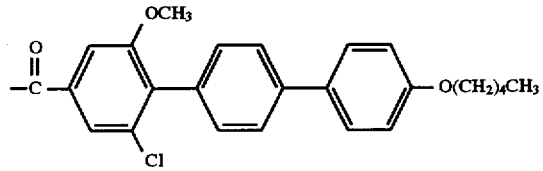

The titled compound was prepared substantially in accordance with the procedure detailed in Example 1, using 300 mg (0.37 mmol) of the compound of the (A-30912A) nucleus (compound of formula IB where R', R" and R'" are each methyl, $R^{x1}$, $R^{x2}$, $R^{y1}$, $R^{y2}$, $R^{y3}$ and $R^{y4}$ are each hydroxy and R° is hydroxy). 200 mg (0.37 mmol) of the compound of Preparation 7 in 35 ml of dimethylformamide.

Yield: 310 mg.

High Res. MS(FAB) for $C_{59}H_{74}N_7O_{18}ClNa$: Calcd: 1226.4677 Found: 1226.4695 (M+Na$^+$)

Example 6

Preparation of the compound of formula I where R', R'' and R''' are each methyl. $R^{x1}$, $R^{x2}$, $R^{y1}$, $R^{y2}$, $R^{y3}$, $R^{y4}$ and R° are each hydroxy and R$^2$ is

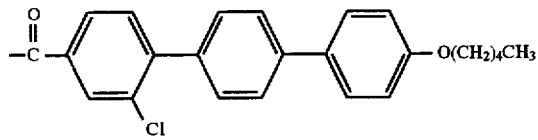

The titled compound was prepared substantially in accordance with the procedure detailed in Example 1, using 1 g (1.25 mmol) of the compound of the (A-30912A) nucleus (compound of formula IB where R', R'' and R''' are each methyl, $R^{x1}$, $R^{x2}$, $R^{y1}$, $R^{y2}$, $R^{y3}$ and $R^{y4}$ are each hydroxy and R° is hydroxy), 0.79 g (1.44 mmol) of the compound of Preparation 8C in 50 ml of dimethylformamide.

Yield: 1 g.

High Res. MS(FAB) for $C_{58}H_{73}N_7O_{17}Cl$: Calcd: 1174.4751 Found: 1174.4752

Example 7

Preparation of the compound of formula I where R', R'' and R''' are each methyl. $R^{x1}$, $R^{x2}$, $R^{y1}$, $R^{y2}$, $R^{y3}$, $R^{y4}$ and R° are each hydroxy and R$^2$ is

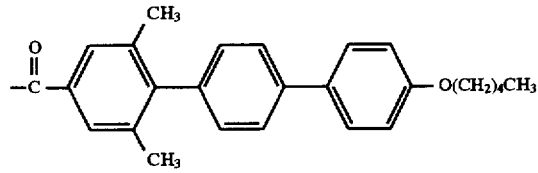

The titled compound was prepared substantially in accordance with the procedure detailed in Example 1, using 1 g (1.25 mmol) of the compound of the (A-30912A) nucleus (compound of formula IB where R', R'' and R''' are each methyl, $R^{x1}$, $R^{x2}$, $R^{y1}$, $R^{y2}$, $R^{y3}$ and $R^{y4}$ are each hydroxy and R° is hydroxy), 0.73 g (1.44 mmol) of the compound of Preparation 9 in 50 ml of dimethylformamide.

Yield: 1 g.

High Res. MS (FAB) for $C_{60}H_{77}N_7O_{17}Li$: Calcd: 1174.5536 Found: 1174.5532 (M+Li)

Example 8

Preparation of the compound of formula I where R', R'' and R''' are each methyl. $R^{x1}$, $R^{x2}$, $R^{y1}$, $R^{y2}$, $R^{y3}$, $R^4$ and R° are each hydroxy and R$^2$ is

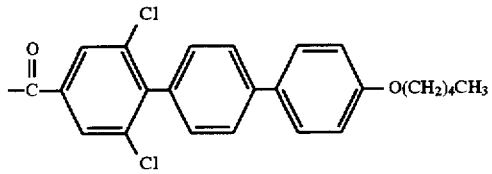

The titled compound was prepared substantially in accordance with the procedure detailed in Example 1, using 1 g (1.25 mmol) of the compound of the (A-30912A) nucleus (compound of formula IB where R', R'' and R''' are each methyl, $R^{x1}$, $R^{x2}$, $R^{y1}$, $R^{y2}$, $R^{y3}$ and $R^{y4}$ are each hydroxy and R° is hydroxy), 0.79 g (1.44 mmol) of the compound of Preparation 10 in 50 ml of dimethylformamide to provide 0.8 g of crude material. This material was purified using HPLC (eluent of 45% acetonitrile in water) to provide 525 mg of the desired titled compound.

High Res. MS(FAB) for $C_{58}H_{71}N_7O_{17}Cl_2Li$: Calcd: 1214.4443 Found: 1214.4457 (M+Li)

Example 9

Preparation of the compound of formula I where R', R'' and R''' are each methyl. $R^{x1}$, $R^{x2}$, $R^{y1}$, $R^{y2}$, $R^{y3}$, $R^{y4}$ and R° are each hydroxy and R$^2$ is

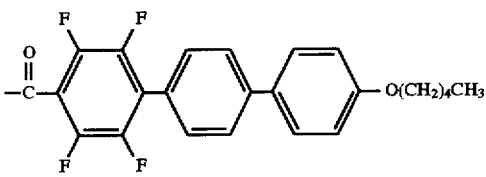

To a suspension containing 2.7 g (6.24 mmol) of the compound of Preparation 11 in 250 ml of methylene chloride, was added 1.15 g (7.5 mmol) of hydroxybenzotriazole hydrate (HOBT.H$_2$O) and 1.55 g (7.5 mmol of dicyclohexylcarbodiimide (DCC). The resultant mixture was reacted over the weekend and then filtered. The resultant filtrate was dried in vacuo to provide a residue. This residue was suspended in diethyl ether and filter to provide 3 g of a solid. The filtrate was dried in vacuo to provide an additional 1.6 g of a solid.

A suspension containing 1 g (1.25 mmol) of the compound of the (A-30912A) nucleus (compound of formula IB where R', R'' and R''' are each methyl, $R^{x1}$, $R^{x2}$, $R^{y1}$, $R^{y2}$, $R^{y3}$ and $R^{y4}$ are each hydroxy and R° is hydroxy) and 1.4 g (0.76 g actual, 1.38 mmol) of the solid prepared above in 100 ml of dimethylformamide was allowed to react at room temperature overnight. The reaction mixture was filtered and then concentrated in vacuo to provide a solid. This solid was combined with diethyl ether and filtered to provide a solid. The resultant solid was washed with methylene chloride, dried and then redissolved in 50 ml of methanol. To this solution was added 75 ml of water and the resultant mixture was acidified with glacial acetic acid resulting in the formation of a precipitate. This precipitate was isolated by filtration, washed with water and dried in vacuo (at 50° C.) to provide 1 g of the desired titled compound.

High Res. MS(FAB) for $C_{58}H_{68}N_7O_{16}F_4$: Calcd: 1194.4659 Found: 1194.4696 (MH−H$_2$O)

Example 10

Preparation of the compound of formula I where R', R" and R'" are each methyl, $R^{x1}$, $R^{x2}$, $R^{y1}$, $R^{y2}$, $R^{y3}$, $R^{y4}$ and R° are each hydroxy and R² is

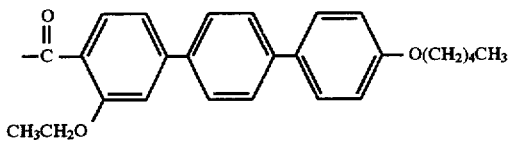

The titled compound was prepared substantially in accordance with the procedure detailed in Example 9, using 1 g (1.25 mmol) of the compound of the (A-30912A) nucleus (compound of formula IB where R', R" and R'" are each methyl, $R^{x1}$, $R^{x2}$, $R^{y1}$, $R^{y2}$, $R^{y3}$ and $R^{y4}$ are each hydroxy and R° is hydroxy) and 0.76 g (0.72 g actual, 1.38 mmol) of a solid [formed from a mixture containing 2.7 g (6.7 mmol) of the compound of Preparation 12, 1.65 g (8 mmol) of DCC and 1.23 g (8 mmol) of HOBT.H$_2$O in 250 ml of methylene chloride] in 50 ml of dimethylformamide.

Yield: 1 g.

High Res. MS(FAB) for $C_{60}H_{77}N_7O_{18}Li$: Calcd: 1190.5485 Found: 1190.5489 (M+Li)

Example 11

Preparation of the compound of formula I where R', R" and R'" are each methyl, $R^{x1}$, $R^{x2}$, $R^{y1}$, $R^{y2}$, $R^{y3}$, $R^{y4}$ and R° are each hydroxy and R² is

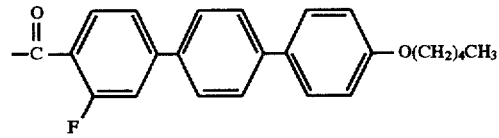

The titled compound was prepared substantially in accordance with the procedure detailed in Example 9, using 1 g (1.25 mmol) of the compound of the (A-30912A) nucleus (compound of formula IB where R', R" and R'" are each methyl, $R^{x1}$, $R^{x2}$, $R^{y1}$, $R^{y2}$, $R^{y3}$ and $R^{y4}$ are each hydroxy and R° is hydroxy) and 0.72 g (0.68 g actual, 1.38 mmol) of a solid [formed from a mixture containing 1.8 g (4.76 mmol) of the compound of Preparation 11, 1.2 g (5.7 mmol) of DCC and 0.87 g (5.7 mmol) of HOBT.H$_2$O in 250 ml of methylene chloride] in 50 ml of dimethylformamide.

Yield: 1 g.

High Res. MS(FAB) for $C_{58}H_{72}N_7O_{17}FLi$: Calcd: 1164.5129 Found: 1164.5248 (M+Li)

The compounds of formula I exhibit antifungal and antiparasitic activity. For example, the compounds of formula I inhibit the growth of various infectious fungi including Candida spp. such as *C. albicans*, *C. parapsilosis*, *C. krusei*, *C. glabrata*, or *C. tropicalis*, *C. lusitaniae*; Torulopus spp. such as *T. glabrata*; Aspergillus spp. such as *A. fumigatus*; Histoplasma spp. such as *H. capsulatum*; Cryptococcus spp. such as *C. neoformans*; Blastomyces spp. such as *B. dermatitidis*; Fusarium spp., Trichophyton spp., *Pseudallescheria boydii*, *Coccidioides immitis*, *Sporothrix schenckii* and the like.

Antifungal activity of a test compound was determined in vitro by obtaining the minimum inhibitory concentration (MIC) of the compound using a standard agar dilution test or a disc-diffusion test. The compound was then tested in vivo (in mice) to determine the effective dose of the test compound for controlling a systemic fungal infection.

Accordingly, the following compounds were tested for antifungal activity against *C. albicans*.

TABLE 1

| Minimal inhibitory concentration against *C. albicans* | |
| --- | --- |
| Example No. | MIC (μg/ml) |
| 1 | 0.01 |
| 2 | 0.02 |
| 3 | 0.039 |
| 4 | 0.01 |
| 5 | 0.02 |
| 6 | 0.02 |
| 7 | 0.039 |
| 8 | 0.039 |
| 9 | 0.02 |
| 10 | 0.039 |
| 11 | 0.005 |

In addition, the effective dose of the following compounds for controlling a systemic fungal infection (*C. albicans*) was tested in vivo (mice).

TABLE 2

| ED$_{50}$ (mouse, i.p.) | |
| --- | --- |
| Example No. | ED$_{50}$ (mg/kg) |
| 1 | 0.45 |
| 2 | 0.39 |
| 3 | 0.72 |
| 4 | 1.9 |
| 5 | >2.5 |
| 6 | >2.5 |
| 7 | 2.5 |
| 8 | >2.5 |
| 9 | 1.25 |
| 10 | >2.5 |
| 11 | 0.99 |

The compounds of the invention also inhibit the growth of certain organisms primarily responsible for opportunistic infections in immunosuppressed individuals. For example the compounds of the invention inhibit the growth of *Pneumocystis carinii* the causative organism of pneumocystis pneumonia (PCP) in AIDS and other immunocompromised patients. Other protozoans that are inhibited by compounds of formula I include Plasmodium spp., Leishmania spp., Trypanosoma spp., Cxyptosporidium spp., Isospora spp., Cyclospora spp., Trichomonas spp., Microsporidiosis spp. and the like.

The compounds of formula I are active in vitro and in vivo and are useful in combating either systemic fungal infections or fungal skin infections. Accordingly, the present invention provides a method of inhibiting fungal activity comprising contacting a compound of formula I, or a pharmaceutically acceptable salt thereof, with a fungus. A preferred method includes inhibiting *Candida albicans* or *Aspergillus fumigatis* activity. The present invention further provides a method of treating a fungal infection which comprises administering an effective amount of a compound of formula I, or a pharmaceutically acceptable salt thereof, to a host in need of such treatment. A preferred method includes treating a *Candida albicans* or *Aspergillus fumigatis* infection.

With respect to antifungal activity, the term "effective amount," means an amount of a compound of the present invention which is capable of inhibiting fungal activity. The dose administered will vary depending on such factors as the nature and severity of the infection, the age and general health of the host and the tolerance of the host to the antifungal agent. The particular dose regimen likewise may vary according to such factors and may be given in a single daily dose or in multiple doses during the day. The regimen may last from about 2–3 days to about 2–3 weeks or longer. A typical daily dose (administered in single or divided doses) will contain a dosage level of from about 0.01 mg/kg to about 100 mg/kg of body weight of an active compound of this invention. Preferred daily doses generally will be from about 0.1 mg/kg to about 60 mg/kg and ideally from about 2.5 mg/kg to about 40 mg/kg.

The present invention also provides pharmaceutical formulations useful for administering the antifungal compounds of the invention. Accordingly, the present invention also provides a pharmaceutical formulation comprising one or more pharmaceutically acceptable carriers, diluents or excipients and a compound of claim 1. The active ingredient in such formulations comprises from 0.1% to 99.9% by weight of the formulation, more generally from about 10% to about 30% by weight. By "pharmaceutically acceptable" it is meant that the carrier, diluent or excipient is compatible with the other ingredients of the formulation and not deleterious to the recipient thereof.

A compound of formula I may be administered parenterally, for example using intramuscular, subcutaneous, or intra-peritoneal injection, nasal, or oral means. In addition to these methods of administration, a compound of formula I may be applied topically for skin infections.

For parenteral administration the formulation comprises a compound of formula I and a physiologically acceptable diluent such as deionized water, physiological saline, 5% dextrose and other commonly used diluents. The formulation may contain a solubilizing agent such as a polyethylene glycol or polypropylene glycol or other known solubilizing agent. Such formulations may be made up in sterile vials containing the antifungal and excipient in a dry powder or lyophilized powder form. Prior to use, a physiologically acceptable diluent is added and the solution withdrawn via syringe for administration to the patient.

The present pharmaceutical formulations are prepared by known procedures using known and readily available ingredients. In making the compositions of the present invention, the active ingredient will generally be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), ointments containing, for example, up to 10% by weight of the active compound, soft and hard gelatin capsules, suppositories, sterile injectable solutions, sterile packaged powders and the like.

For oral administration, the antifungal compound is filled into gelatin capsules or formed into tablets. Such tablets may also contain a binding agent, a dispersant or other suitable excipients suitable for preparing a proper size tablet for the dosage and particular antifungal compound of the formula I. For pediatric or geriatric use the antifungal compound may be formulated into a flavored liquid suspension, solution or emulsion. A preferred oral formulation is linoleic acid, cremophor RH-60 and water and preferably in the amount (by volume) of 8% linoleic acid, 5% cremophor RH-60, 87% sterile water and a compound of formula I in an amount of from about 2.5 to about 40 mg/ml.

For topical use the antifungal compound may be formulated with a dry powder for application to the skin surface or it may be formulated in a liquid formulation comprising a solubilizing aqueous liquid or non-aqueous liquid, e.g., an alcohol or glycol.

The following formulation examples are illustrative only and are not intended to limit the scope of the invention in any way. The term "active ingredient" means a compound according to formula I or a pharmaceutically acceptable salt thereof.

Formulation 1

Hard gelatin capsules are prepared using the following ingredients:

|  | Quantity (mg/capsule) |
|---|---|
| Active ingredient | 250 |
| Starch, dried | 200 |
| Magnesium stearate | 10 |
| Total | 460 mg |

Formulation 2

A tablet is prepared using the ingredients below:

|  | Quantity (mg/capsule) |
|---|---|
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight |
|---|---|
| Active ingredient | 0.25 |
| Methanol | 25.75 |
| Propellant 22 | 74.00 |
| (Chlorodifluoromethane) | |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

| | |
|---|---|
| Active ingredient | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinyl-pyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

| | |
|---|---|
| Active ingredient | 80 mg |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| | |
|---|---|
| Active ingredient | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 ml dose, are made as follows:

| | |
|---|---|
| Active ingredient | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup Lo form a smooth paste. The benzoic acid solution, flavor and color are diluted with a portion of the water and added, with stirring. Sufficient water is then added to produce the required volume.

Formulation 8

An intravenous formulation may be prepared as follows:

| | |
|---|---|
| Active ingredient | 100 mg |
| Isotonic saline | 1,000 ml |

The solution of the above ingredients generally is administered intravenously to a subject at a rate of 1 ml per minute.

The present invention further provides a method for treating or preventing the onset of Pneumocystis pneumonia in a host susceptible to Pneumocystis pneumonia which comprises administering an effective amount of a compound of formula I, or a pharmaceutically acceptable salt thereof, to a host in need of such treatment. The compounds of formula I can be used prophylactically to prevent the onset of the infection which is caused by the organism Pneumocystis carinii, or alternatively they can be used to treat a host that has been infected with P. carinii. A compound of formula I may be administered parenterally, for example using intramuscular, intravenous or intra-peritoneal injection, orally or by inhaling directly into the airways of the lungs. A preferred mode of administration is inhalation of an aerosol spray formulation of a compound of formula I.

With respect to antiparasitic activity, the term "effective amount," means an amount of a compound of the present invention which is capable of inhibiting parasitic activity. An effective amount of the compound of formula I is from about 3 mg/kg of patient body weight to about 100 mg/kg. The amount administered may be in a single daily dose or multiple doses of, for example, two, three or four times daily throughout the treatment regimen. The amount of the individual doses, the route of delivery, the frequency of dosing and the term of therapy will vary according to such factors as the intensity and extent of infection, the age and general health of the patient, the response of the patient to therapy and how well the patient tolerates the drug. It is known that Pneumocystis pneumonia infections in AIDS patients are highly refractory owing to the nature of the infection. For example, in severe, advanced infections the lumenal surface of the air passages becomes clogged with infectious matter and extensive parasite development occurs in lung tissue. A patient with an advanced infection will accordingly require higher doses for longer periods of time. In contrast, immune deficient patients who are not severely infected and who are susceptible to Pneumocystis pneumonia can be treated with lower and less frequent prophylactic doses.

We claim:
1. A compound of the formula:

[Structure I shown with substituents R', R", R'", R, R$^{x1}$, R$^{y1}$, R$^{y2}$, R$^{y3}$, R$^{y4}$, R$^{x2}$, R$^0$, R$^2$]

wherein:

R' is hydrogen, methyl or —CH$_2$C(O)NH$_2$;

R" and R'" are independently methyl or hydrogen;

R$^{x1}$ is hydrogen, hydroxy or —O—R;

R is C$_1$–C$_6$ alkyl, benzyl, —(CH$_2$)$_2$Si(CH$_3$)$_3$, —CH$_2$CHOHCH$_2$OH, —CH$_2$CH=CH$_2$, —(CH$_2$)$_a$COOH, —(CH$_2$)$_b$NR$^{z1}$R$^{z2}$, —(CH$_2$)$_c$POR$^{z3}$R$^{z4}$ or —[(CH$_2$)$_2$O]$_d$—(C$_1$–C$_6$)alkyl;

a, b and c are independently 1, 2, 3, 4, 5 or 6;

R$^{z1}$ and R$^{z2}$ are independently hydrogen, C$_1$–C$_6$ alkyl, or R$^{z1}$ and R$^{z2}$ combine to form —CH$_2$(CH$_2$)$_e$CH$_2$—;

R$^{z3}$ and R$^{z4}$ are independently hydroxy or C$_1$–C$_6$ alkoxy;

d is 1 or 2;

e is 1, 2 or 3;

R$^{x2}$, R$^{y1}$, R$^{y2}$, R$^{y3}$ and R$^{y4}$ are independently hydroxy or hydrogen;

R$^0$ is hydroxy, —OP(O) (OH)$_2$ or a group of the formulae:

$$-O-\overset{O}{\underset{OH}{P}}-R^1 \quad \text{or} \quad -O-\overset{O}{\underset{OH}{P}}-OR^1;$$

R$^1$ is C$_1$–C$_6$ alkyl, phenyl, p-halo-phenyl, p-nitrophenyl, benzyl, p-halo-benzyl or p-nitro-benzyl;

R$^2$ is

[Structure showing —C(O)-biphenyl-R$^3$ with (R$^{2a}$)$_a$ substituents]

each R$^{2a}$ is independently hydroxy, halo, nitro, amino, trifluoromethyl, C$_1$–C$_6$ alkyl, C$_1$–C$_6$ alkoxy or C$_1$–C$_6$ alkylthio;

a is 1, 2, 3 or 4;

R$^3$ is C$_1$–C$_{12}$ alkyl, C$_1$–C$_{12}$ alkoxy or —O—(CH$_2$)$_m$—[O—(CH$_2$)$_n$]$_p$—O—(C$_1$–C$_{12}$ alkyl);

m is 2, 3 or 4;

n is 2, 3 or 4; and p is 0 or 1;

or a pharmaceutically acceptable salt thereof.

2. A compound according to claim 1 where:

R', R" and R'" are each methyl;

R$^{y1}$, R$^{y2}$, R$^{y3}$ and R$^{y4}$ are each hydroxy;

R$^{x1}$ is hydrogen, hydroxy or —O—R;

R is methyl, benzyl, —CH$_2$CHOHCH$_2$OH, —(CH$_2$)$_b$NR$^{z1}$R$^{z2}$ or —(CH$_2$)$_2$POR$^{z3}$R$^{z4}$;

b is 2, 3, 4, 5 or 6;

R$^{z1}$ and R$^{z2}$ are independently hydrogen or C$_1$–C$_4$ alkyl;

R$^{z3}$ and R$^{z4}$ are independently hydroxy or methoxy;

R$^{x2}$ is hydrogen or hydroxy;

R$^0$ is hydroxy, —OP(O) (OH)$_2$ or a group of the formulae:

$$-O-\overset{O}{\underset{OH}{P}}-R^1 \quad \text{or} \quad -O-\overset{O}{\underset{OH}{P}}-OR^1;$$

R$^1$ is methyl;

or a pharmaceutically acceptable salt thereof.

3. A compound according to claim 2 where:

R$^{x1}$ is hydrogen or hydroxy;

R$^{x2}$ is hydrogen or hydroxy;

R$^0$ is hydroxy;

a is 1 or 2;

R$^{2a}$ is halo, C$_1$–C$_6$ alkyl or C$_1$–C$_6$ alkoxy;

R$^3$ is C$_1$–C$_{12}$ alkoxy or —O—(CH$_2$)$_2$—O—(C$_1$–C$_{12}$ alkyl);

or a pharmaceutically acceptable salt thereof.

4. The compound according to claim 3 where:

R$^{x1}$ is hydroxy;

R$^{x2}$ is hydroxy;

a is 1;

R$^{2a}$ is methyl, chloro, fluoro or methoxy; and

R$^3$ is C$_1$–C$_6$ alkoxy;

or a pharmaceutically acceptable salt thereof.

5. A compound according to claim 4 which is R$^2$ is

[Structure showing —C(O)-biphenyl-R$^3$ with R$^{2a}$]

R$^{2a}$ is methyl, chloro or fluoro;

or a pharmaceutically acceptable salt thereof.

6. A pharmaceutical formulation comprising one or more pharmaceutically acceptable carriers, diluents or excipients and a compound of claim 1.

7. A pharmaceutical formulation according to claim 6 where the compound is one where:

R', R" and R'" are each methyl;

R$^{y1}$, R$^{y2}$, R$^{y3}$ and R$^{y4}$ are each hydroxy;

R$^{x1}$ is hydrogen, hydroxy or —O—R;

R is methyl, benzyl, —CH$_2$CHOHCH$_2$OH, —(CH$_2$)$_b$NR$^{z1}$R$^{z2}$ or —(CH$_2$)$_2$POR$^{z3}$R$^{z4}$;

b is 2, 3, 4, 5 or 6;

R$^{z1}$ and R$^{z2}$ are independently hydrogen or C$_1$–C$_4$ alkyl;

R$^{z3}$ and R$^{z4}$ are independently hydroxy or methoxy;

$R^{x2}$ is hydrogen or hydroxy;
$R^o$ is hydroxy, —OP(O)(OH)$_2$ or a group of the formulae:

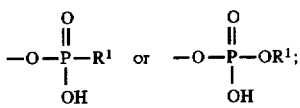

$R^1$ is methyl;
or a pharmaceutically acceptable salt thereof.

8. A pharmaceutical formulation according to claim 7 where the compound is one where:
$R^{x1}$ is hydrogen or hydroxy;
$R^{x2}$ is hydrogen or hydroxy;
$R^o$ is hydroxy;
a is 1 or 2;
$R^{2a}$ is halo, $C_1$-$C_6$ alkyl or $C_1$-$C_6$ alkoxy;
$R^3$ is $C_1$-$C_{12}$ alkoxy or —O—(CH$_2$)$_2$—O—($C_1$-$C_{12}$ alkyl);
or a pharmaceutically acceptable salt thereof.

9. A pharmaceutical formulation according to claim 8 where the compound is one where:
$R^{x1}$ is hydroxy;
$R^{x2}$ is hydroxy;
a is 1;
$R^{2a}$ is methyl, chloro, fluoro or methoxy; and
$R^3$ is $C_1$-$C_6$ alkoxy;
or a pharmaceutically acceptable salt thereof.

10. A pharmaceutical formulation according to claim 9 where the compound is one where:
$R^2$ is

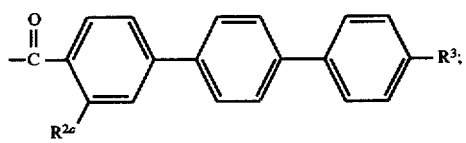

$R^{2a}$ is methyl, chloro or fluoro;
or a pharmaceutically acceptable salt thereof.

11. A method of inhibiting fungal activity comprising contacting a compound of claim 1 with a fungus.

12. A method according to claim 11 where the compound is one where:
R', R" and R'" are each methyl;
$R^{y1}$, $R^{y2}$, $R^{y3}$ and $R^{y4}$ are each hydroxy;
$R^{x1}$ is hydrogen, hydroxy or —O—R;
R is methyl, benzyl, —CH$_2$CHOHCH$_2$OH, —(CH$_2$)$_b$NR$^{z1}$R$^{z2}$ or —(CH$_2$)$_2$POR$^{z3}$R$^{z4}$;
b is 2, 3, 4, 5 or 6;
$R^{z1}$ and $R^{z2}$ are independently hydrogen or $C_1$-$C_4$ alkyl;
$R^{z3}$ and $R^{z4}$ are independently hydroxy or methoxy;
$R^{x2}$ is hydrogen or hydroxy;
$R^o$ is hydroxy, —OP(O)(OH)$_2$ or a group of the formulae:

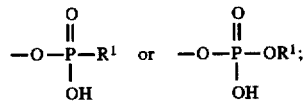

$R^1$ is methyl;
or a pharmaceutically acceptable salt thereof.

13. A method according to claim 12 where the compound is one where:
$R^{x1}$ is hydrogen or hydroxy;
$R^{x2}$ is hydrogen or hydroxy;
$R^o$ is hydroxy;
a is 1 or 2;
$R^{2a}$ is halo, $C_1$-$C_6$ alkyl or $C_1$-$C_6$ alkoxy;
$R^3$ is $C_1$-$C_{12}$ alkoxy or —O—(CH$_2$)$_2$—O—($C_1$-$C_{12}$ alkyl);
or a pharmaceutically acceptable salt thereof.

14. A method according to claim 13 where the compound is one where:
$R^{x1}$ is hydroxy;
$R^{x2}$ is hydroxy;
a is 1;
$R^{2a}$ is methyl, chloro, fluoro or methoxy; and
$R^3$ is $C_1$-$C_6$ alkoxy;
or a pharmaceutically acceptable salt thereof.

15. A method according to claim 14 where the compound is one where:
$R^2$ is

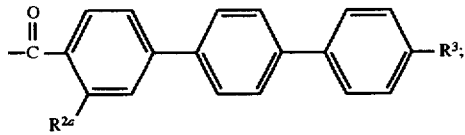

$R^{2a}$ is methyl, chloro or fluoro;
or a pharmaceutically acceptable salt thereof.

16. A method of treating a fungal infection which comprises administering an effective amount of a compound of claim 1 to a host in need of such treatment.

17. A method according to claim 16 where the compound is one where:
R', R" and R'" are each methyl;
$R^{y1}$, $R^{y2}$, $R^{y3}$ and $R^{y4}$ are each hydroxy;
$R^{x1}$ is hydrogen, hydroxy or —O—R;
R is methyl, benzyl, —CH$_2$CHOHCH$_2$OH, —(CH$_2$)$_b$NR$^{z1}$R$^{z2}$ or —(CH$_2$)$_2$POR$^{z3}$R$^{z4}$;
b is 2, 3, 4, 5 or 6;
$R^{z1}$ and $R^{z2}$ are independently hydrogen or $C_1$-$C_4$ alkyl;
$R^{z3}$ and $R^{z4}$ are independently hydroxy or methoxy;
$R^{x2}$ is hydrogen or hydroxy;
$R^o$ is hydroxy, —OP(O)(OH)$_2$ or a group of the formulae:

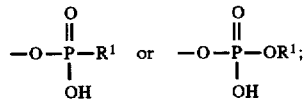

$R^1$ is methyl;
or a pharmaceutically acceptable salt thereof.

18. A method according to claim 17 where the compound is one where:
$R^{x1}$ is hydrogen or hydroxy;
$R^{x2}$ is hydrogen or hydroxy;
$R^o$ is hydroxy;
a is 1 or 2;
$R^{2a}$ is halo, $C_1$-$C_6$ alkyl or $C_1$-$C_6$ alkoxy;
$R^3$ is $C_1$-$C_{12}$ alkoxy or —O—(CH$_2$)$_2$—O—($C_1$-$C_{12}$ alkyl);

or a pharmaceutically acceptable salt thereof.

19. A method according to claim 18 where the compound is one where:

$R^{x1}$ is hydroxy;
$R^{x2}$ is hydroxy;
a is 1;
$R^{2a}$ is methyl, chloro, fluoro or methoxy; and
$R^3$ is $C_1$–$C_6$ alkoxy;

or a pharmaceutically acceptable salt thereof.

20. A method according to claim 19 where the compound is one where:

$R^2$ is

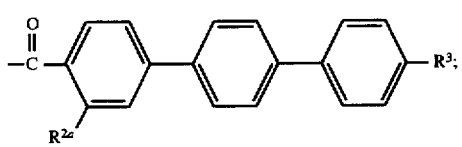

$R^{2a}$ is methyl, chloro or fluoro;
or a pharmaceutically acceptable salt thereof.

21. A method for inhibiting parasitic activity comprising contacting a compound of claim 1 with a parasite.

22. A method according to claim 21 where the compound is one where:

R', R" and R''' are each methyl;
$R^{y1}$, $R^{y2}$, $R^{y3}$ and $R^{y4}$ are each hydroxy;
$R^{x1}$ is hydrogen, hydroxy or —O—R;
R is methyl, benzyl, —CH$_2$CHOHCH$_2$OH, —(CH$_2$)$_b$NR$^{z1}$R$^{z2}$ or —(CH$_2$)$_2$POR$^{z3}$R$^{z4}$;
b is 2, 3, 4, 5 or 6;
$R^{z1}$ and $R^{z2}$ are independently hydrogen or $C_1$–$C_4$ alkyl;
$R^{z3}$ and $R^{z4}$ are independently hydroxy or methoxy;
$R^{x2}$ is hydrogen or hydroxy;
$R^o$ is hydroxy, —OP(O)(OH)$_2$ or a group of the formulae:

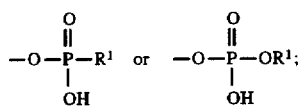

$R^1$ is methyl;
or a pharmaceutically acceptable salt thereof.

23. A method according to claim 22 where the compound is one where:

$R^{x1}$ is hydrogen or hydroxy;
$R^{x2}$ is hydrogen or hydroxy;
$R^o$ is hydroxy;
a is 1 or 2;
$R^{2a}$ is halo, $C_1$–$C_6$ alkyl or $C_1$–$C_6$ alkoxy;
$R^3$ is $C_1$–$C_{12}$ alkoxy or —O—(CH$_2$)$_2$—O—($C_1$–$C_{12}$ alkyl);

or a pharmaceutically acceptable salt thereof.

24. A method according to claim 23 where the compound is one where:

$R^{x1}$ is hydroxy;
$R^{x2}$ is hydroxy;
a is 1;
$R^{2a}$ is methyl, chloro, fluoro or methoxy; and
$R^3$ is $C_1$–$C_6$ alkoxy;

or a pharmaceutically acceptable salt thereof.

25. A method according to claim 24 where the compound is one where:

$R^2$ is

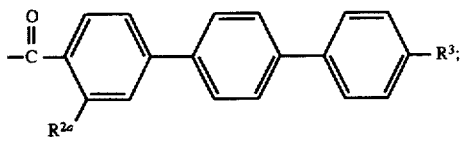

$R^{2a}$ is methyl, chloro or fluoro;
or a pharmaceutically acceptable salt thereof.

26. A method for treating or preventing the onset of Pneumocystis pneumonia in a host susceptible to Pneumocystis pneumonia which comprises administering an effective amount of a compound of formula I, or a pharmaceutically acceptable salt thereof, to a host in need of such treatment.

27. A method according to claim 26 where the compound is one where:

R', R" and R''' are each methyl;
$R^{y1}$, $R^{y2}$, $R^{y3}$ and $R^{y4}$ are each hydroxy;
$R^{x1}$ is hydrogen, hydroxy or —O—R;
R is methyl, benzyl, —CH$_2$CHOHCH$_2$OH, —(CH$_2$)$_b$NR$^{z1}$R$^{z2}$ or —(CH$_2$)$_2$POR$^{z3}$R$^{z4}$;
b is 2, 3, 4, 5 or 6;
$R^{z1}$ and $R^{z2}$ are independently hydrogen or $C_1$–$C_4$ alkyl;
$R^{z3}$ and $R^{z4}$ are independently hydroxy or methoxy;
$R^{x2}$ is hydrogen or hydroxy;
$R^o$ is hydroxy, —OP(O)(OH)$_2$ or a group of the formulae:

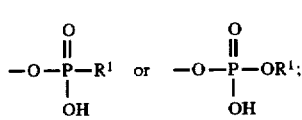

$R^1$ is methyl;
or a pharmaceutically acceptable salt thereof.

28. A method according to claim 27 where the compound is one where:

$R^{x1}$ is hydrogen or hydroxy;
$R^{x2}$ is hydrogen or hydroxy;
$R^o$ is hydroxy;
a is 1 or 2;
$R^{2a}$ is halo, $C_1$–$C_6$ alkyl or $C_1$–$C_6$ alkoxy;
$R^3$ is $C_1$–$C_{12}$ alkoxy or —O—(CH$_2$)$_2$—O—($C_1$–$C_{12}$ alkyl);

or a pharmaceutically acceptable salt thereof.

29. A method according to claim 28 where the compound is one where:

$R^{x1}$ is hydroxy;
$R^{x2}$ is hydroxy;
a is 1;
$R^{2a}$ is methyl, chloro, fluoro or methoxy; and
$R^3$ is $C_1$–$C_6$ alkoxy;

or a pharmaceutically acceptable salt thereof.

30. A method according to claim 29 where the compound is one where:

R² is
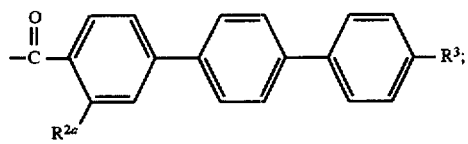
R²ᵃ is methyl, chloro or fluoro;
or a pharmaceutically acceptable salt thereof.
* * * * *